(12) United States Patent
Humayun et al.

(10) Patent No.: US 7,217,263 B2
(45) Date of Patent: May 15, 2007

(54) DEVICE AND METHOD FOR MANUAL RETINAL VEIN CATHETERIZATION

(75) Inventors: Mark S. Humayun, Timonium, MD (US); Patrick S. Jensen, Issaquah, WA (US); Terry H. Shelley, Hampstead, MD (US); Gildo Y. Fujii, Baltimore, MD (US); Hany S. Hamza, Cairo (EG); Aaron C. Barnes, Columbia, MD (US); Eugene deJuan, Jr., Phoenix, MD (US)

(73) Assignee: The Johns Hopkins University, Baltimore, MD (US)

( * ) Notice: Subject to any disclaimer, the term of this patent is extended or adjusted under 35 U.S.C. 154(b) by 113 days.

(21) Appl. No.: 09/754,094

(22) Filed: Jan. 3, 2001

(65) Prior Publication Data

US 2002/0002362 A1    Jan. 3, 2002

Related U.S. Application Data

(60) Provisional application No. 60/217,468, filed on Jul. 11, 2000, provisional application No. 60/174,260, filed on Jan. 3, 2000.

(51) Int. Cl.
*A61M 25/00*    (2006.01)
*A61M 5/32*    (2006.01)
(52) U.S. Cl. .................. 604/523; 604/524; 604/272
(58) Field of Classification Search ............... 604/264, 604/521, 272, 500, 93.01, 161, 523, 524, 604/525, 530; 606/4, 15, 44
See application file for complete search history.

(56) References Cited

U.S. PATENT DOCUMENTS

| 4,191,176 | A |   | 3/1980 | Spina et al. |
| 5,234,406 | A | * | 8/1993 | Drasner et al. ............. 604/512 |
| 5,364,374 | A |   | 11/1994 | Morrison et al. |
| 5,545,153 | A | * | 8/1996 | Grinblat et al. ............. 604/294 |
| 5,792,099 | A | * | 8/1998 | DeCamp et al. ............ 604/506 |
| 5,891,084 | A |   | 4/1999 | Lee |
| 5,947,296 | A | * | 9/1999 | Castora ..................... 206/571 |
| 6,355,027 | B1 | * | 3/2002 | Le et al. .................... 604/525 |
| 6,402,734 | B1 | * | 6/2002 | Weiss ........................ 604/521 |

FOREIGN PATENT DOCUMENTS

WO    WO 00/01367    1/2000

OTHER PUBLICATIONS

PCT Search Report.

* cited by examiner

*Primary Examiner*—Catherine S. Williams
(74) *Attorney, Agent, or Firm*—Edwards Angell Palmer & Dodge LLP; Peter F. Corless; Lisa Swiszcz Hazzard

(57) ABSTRACT

A microcatheter system that allows for vascular infusion into retinal veins for extended periods of time. The microcatheter system includes a flexible cannula that is inserted into the retinal vein lumen and that remains stably within the retinal vein lumen without being held by a robot, micromanipulator or similar holding devices. The microcatheter system is particularly suitable for the treatment of retinal venous occlusive disease.

54 Claims, 9 Drawing Sheets

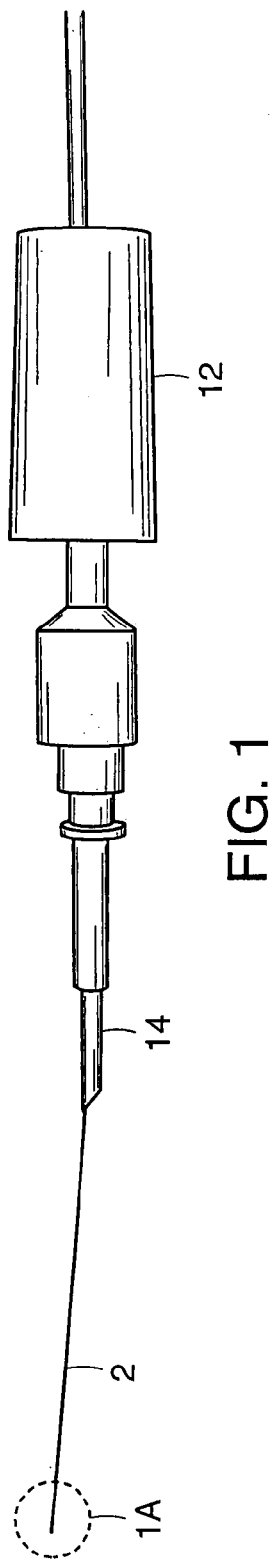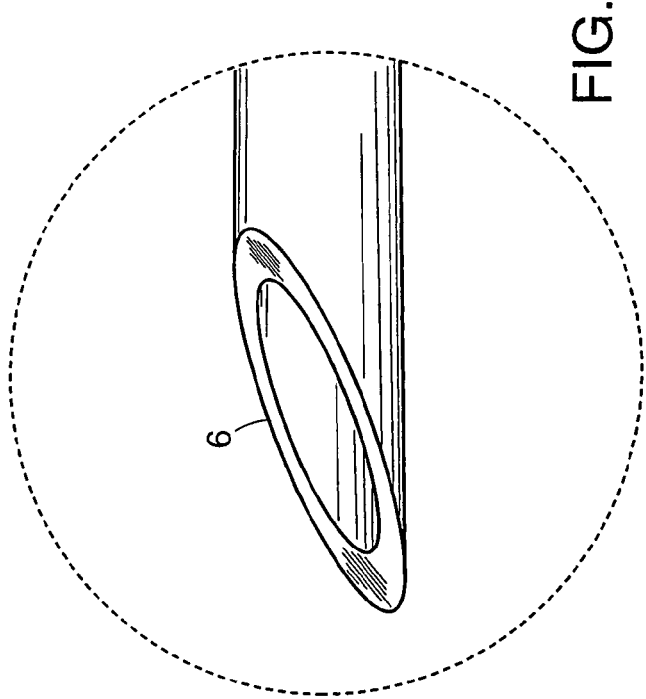

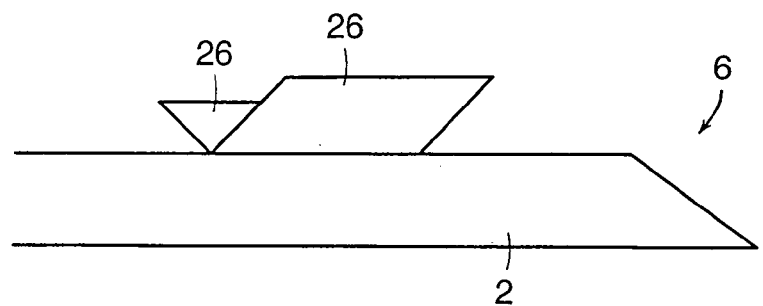
FIG. 2
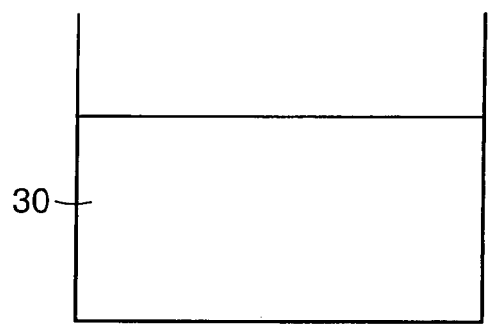
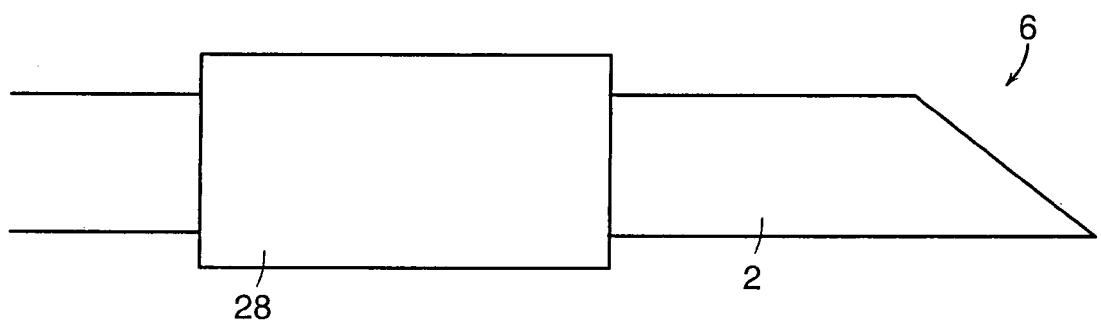
FIG. 3

ID AND METHOD FOR MANUAL
RETINAL VEIN CATHETERIZATION

The present application claims the benefit of U.S. provisional application No. 60/174,260, filed on Jan. 3, 2000; and U.S. provisional application No. 60/217,468, filed on Jul. 11, 2000, both of which applications are incorporated herein by reference in their entirety.

FIELD OF THE INVENTION

The present invention relates to improved microcatheter devices. More particularly, the present invention relates to a flexible microcatheter instrument and surgical technique that allows for vascular infusion into retinal veins for extended periods of time. The device and method are particularly suitable for the treatment of retinal venous occlusive disease.

BACKGROUND OF THE INVENTION

Retinal vascular occlusions are a leading cause of blindness in elderly patients. While younger patients may develop this disease (referred to as papillophlebitis in younger patients), most occlusions occur in individuals over the age of 50.

A retinal vascular occlusion is characterized by a fully or partially occluded retinal vessel that limits the flow of blood through the retinal tissue. Blood is delivered to the retina through the arteries, which then lead to the capilliaries and then the venous system beginning with smaller veins and ending with larger veins, and finally to the central retinal vein. Occlusion in any of these retinal vessels leads to a build-up of pressure, which may lead to hemorrhages and also leakage of fluid and other constituents of blood.

The site of the occlusion typically occurs on the venous side and may occur in either the branch vessel (branch retinal vein occlusion—BRVO) or in the central retinal vein (central retinal vein occlusion—CRVO). The occlusion site determines the extent of the hemorrhage: a small vein branch occlusion to a quadrantic occlusion affects one fourth of the retina, a hemispheric or hemi-retinal occlusion affects one half of the retina, and a central retinal vein occlusion (CRVO) affects the entire retina.

Retinal venous occlusive disease can affect vision in many ways. The retina is made up seven layers of cells that convert light signals into a neural signals. The cells that transmit to the brain are the ganglion cells. In order for the ganglion cells to function properly, they require an adequate flow of blood. When retinal vessels are blocked, the area of the retina supplied by that vessel has poor blood flow, which results in sub-optimal performance by the local ganglion cells and even death of these local ganglion cells. In some severe cases, poor blood flow resulting from retinal vascular occlusions can also lead to the development of abnormal new vessels (neovascularization). These new vessels are fragile and leak fluid and blood, which damages cells in the retina. In severe cases of neovacularization, the new abnormal blood vessels may pull on the retina, leading to retinal detachment. In very serious cases, the eye may develop neovascular glaucoma, in which fluid outflow channels in the eye are blocked, placing the eye is under very high pressure. This may result in severe vision loss, pain and even loss of the eye itself.

Although retinal venous occlusive disease is a highly prevalent disease with serious consequences, treatment options remain limited.

The Central Vein Occlusion Study provides guidelines to treat the sequelae of the venous obstruction rather than the underlying occlusive event. ("'Natural history and clinical management of central retinal vein occlusion. The Central Vein Occlusion Study Group" *Arch. Ophthalmol*, 1997:115: 486–91. Several recent efforts have had the goal to re-establish vent outflow. One such effort proposes to bypass the occluded vein by a laser or surgically-induced chorioretinal anastomosiss. (Fekrat S. de J E, Jr. "Chorioretinal venous anastomosis for central retinal vein occlusion transvitreal venipuncture" *Ophthalmic Surg. Lasers*, 1995; 113: 456–62; McAllister I L, Constable 1 J. "Laser-induced chorioretinal venous anastomosis for treatment of nonischemic centrl retinal vein occlusion" *Arch. Ophthalmol*, 1995:113:456–62.) This approach does not attempt to re-establish the normal venous return pathway from the retina. Moreover, it has had limited success and can lead to uncontrolled choroidal neovascularization resulting in vitreous hemorrhage and tractional retinal detachment. (McAllister I L, Douglas J P, Constable 1 J, Yu D Y. "Laser induced chorioretinal venous anastomosis for nonischemic central retinal vein occlusion: evaluation of the complications and their risk factors" *Am. J Ophthalmol*, 1998; 126:219–29). Similarly, the benefit of other approaches remain unproven such as, for example, the use of platelet inhibitors (Glacet-Bernard A. Coscas G. Chabanel A, Zourdani A, Lelong F. Samama M M. "A randomized, double-masked study on the treatment of retinal vein occlusion with troxerutin" *Am. J. Ophthalmol*,. 1994; 118:421–29), steroids (Beaumont P E, Kang H K. "Ophthalmodynamometry and corticosteroids in central retinal vein occlusion" *Aust. N. Z. J. Ophthalmol*, 1994:22:271–74), hemodilution (Wolf S, Arend O, Bertram B, Remky A, Schulte K, Wald K J et al. "Hemodilution therapy in central retinal vein occlusion, One-year results of a prospective randomized study" *Graefes Arch. Clin. Exp. Ophthalmol*, 1994:232:33–39; Luckie A P, Wroblewski J J, Hamilton P, Bird A C, Sanders M, Slater N et al. "A randomised prospective study of outpatient haemodilution for central retinal vein obstruction" *Aust N. Z. J Ophthalmol*, 1996; 24:223 32), or optic nerve sheath decompression (Dev S, Buckley E G. "Optic nerve sheath decompression for progressive central retinal vein occlusion" *Ophthalmic Surg. Lasers*, 1999; 30:181–84).

A histopathologic study of 29 human eyes with ischemic central retinal vein occlusions concluded that the underlying cause of venous occlusions was a venous thrombosis in the region of lamina cribosa. (Green W R, Chan C C, Hutchins G M, Terry J M. "Central retinal vein occlusion: a prospective histopathologic study of 29 eyes in 28 cases" *Trans. Am. Ophthalmol Soc.*, 1981:79:371–422). Clot dissolving drugs called thrombolytic agents exist and are used successfully on other occluded vascular networks. Because thrombolytics are effective in treating venous thrombosis elsewhere in the body, the idea of systemic administration of these drugs for the treatment of retinal venous occlusions is attractive. However, studies involving the systemic use of thrombolytics to treat central retinal vein occlusions have not been substantiated. (See, e.g. Elman M J. "Thrombolytio therapy for central retinal vein occlusion: results of a pilot study" *Trans. Am. Ophthalmol Soc.*, 1998; 94:471–504; Kohner E M, Pettit J E, Hamilton A M, Bulpitt C J, Dollery C T. "Streptokinase in central retinal vein occlusion: a controlled clinical trial" *Br. Med. J.*, 1976; 1:550–53; Hattenbach L O. "Systemic lysis therapy in retinal vascular occlusions" *Ophthalmologe*, 1998 95:568–75; Hattenbach L O, Wellermann G. Steinkarnp G W, Scharrer I, Koch F H, Ohrloff C. "Visual outcome after treatment with low-dose recombinant tissue plasminogen activator or hemodilution in ischemic central retinal vein occlusion" *Ophthalmologe,* 1998 95:568–75; Hattenbach L O, Wellermann G. Steinkarnp G W, Scharrer I, Koch F H, Ohrloff C. "Visual outcome after treatment with low-dose recombinant tissue plasminogen activator or hemodilution in ischemic central retinal vein occlusion" *Ophthalmologica,* 1999; 213; 360–66). The vasculature of the retina is unique, consisting of very long vessels emanating from and returning to a single point of entry in the optic verve. When presented with a static column of blood, thrombolytic agents delivered systemically are not able to diffuse through the vessels and arrive at the clot site in sufficient doses to dissolve the clot. If the systemic does is increased to a level that may potentially dissolve the clot, hemorrhage and other complications including stroke and death may occur. Thus, the potential promise of systemic thrombolysis must be soberly balanced with the risk of a life-threatening central nervous system or gastrointestinal hemorrhage.

An alternate method of administering thrombolytic therapy is to deliver the drug locally at or near the site of the occluded retinal vein by means of a microcatheter placed in the affected retinal vein. The idea of retinal vein catheterization for local intravascular thrombolytic delivery is not new and is found in the literature since at least 1987. (See, e.g. Allf B E, de J E, Jr. "In vivo cannulation of retinal vessels" *Dev. Ophthalmol,* 1987; 225:221–25; Cunha-Vaz J G, Murta J N, Proenca R D. "Micropuncture of retinal vessels" *Dev. Ophthalmol,* 1989; 18:90–94; Glucksberg M R, Dunn R, Glebs C P. "In vivo micropuncture of retinal vessels" *Graefes Arch. Clin. Exp. Ophthalmol,* 1993; 231: 405–07; Weiss J N. "Treatment of central retinal vein occlusion by injection of tissue plasminogen activator into a retinal vein" *Am. J Ophthalmol* 1998; 126:142–44; Tang W M, Han D P. "A study of surgical approaches to retinal vascular occlusions" *Arch. Ophthalmol,* 2000:11 8:136–43; Weiss J N. "Retinal surgery for treatment of central retinal vein occlusion" *Ophthalmic Surg. Lasers,* 2000; 31:162–65). This approach has the theoretical advantage of allowing local infusion of a significantly smaller volume of a highly concentrated thrombolytic, thus reducing the systemic risk of a hemorrhage and reducing the risk of inducing a systemic fibrinolytic state.

However, the technique and instrumentation required to reliably insert a cannula into the lumen of a retinal vessel has been daunting. Further, as is the case for effective thrombolysis elsewhere in the body, the thrombolytic cascade of TPA, streptolinase or urikinase takes about 30 minutes to complete. Thus, the thrombolytic must be infused at least 30 minutes if not longer to be effective. (See. e.g. Goldhaber S Z. "Thrombolytic therapy" *Adv. Intern. Med,* 1999; 44:311–25; Heinz M, Theiss W. "Thrombolytic therapy of venous thromboses" *Internist (Berl),* 1996:37:567–73; Gulba D C, Bode C, Runge M S, Huber K. "Thrombolytic agents—an overview" *Ann. Hematal,* 1996; 73 Suppl 1:S9–27; Kandarpa K. "Catheter-directed thrombolysis of peripheral arterial occlusions and deep vein thrombosis" *Thromb. Haemost.,* 1999; 82:987–96; Comerota A J, Katz M L, White J V. "Thrombolytic therapy for acute deep venous thrombosis: how much is enough?" *Cardiovasc. Surg.,* 1996; 4:101–04).

The need for a long-term infusion into a retinal vein and the manual dexterity required to cannulate vessels of diameters as small as the retinal vein has led to the use of a rigid cannulae held in place by hand or with the use of a robot or a micromanipulator, which provide a mechanical aid to keep the instrument in place during and after the retinal venous puncture. (See. e.g. Goldhaber S Z. "Thrombolytic therapy" *Adv. Intern. Med.,* 1999; 44:311–25; Heinz M, Theiss W. "Thrombolytic therapy of venous thromboses" *Internist (Berl),* 1996:37:567–73; Gulba D C, Bode C, Runge M S, Huber K. "Thrombolytic agents—an overview" *Ann. Hematal.,* 1996; 73 Suppl 1:S9–27; Kandarpa K. "Catheter-directed thrombolysis of peripheral arterial occlusions and deep vein thrombosis" *Thromb. Haemost.,* 1999; 82:987–96; Comerota A J, Katz M L, White J V. "Thrombolytic therapy for acute deep venous thrombosis: how much is enough?" *Cardiovasc, Surg.,* 1996; 4:101–04; Allf B E, de J E, Jr. "In vivo cannulation of retinal vessels" *Dev. Ophthalmol,* 1987; 225:221–25; Cunha-Vaz J G, Murta J N, Proenca R D. "Micropuncture of retinal vessels" *Dev. Ophthalmol,* 1989; 18:90–94; Glucksberg M R, Dunn R, Glebs C P. "In vivo micropuncture of retinal vessels" *Graefes Arch. Clin. Exp. Ophthalmol,* 1993; 231:405–07; Weiss J N. "Treatment of central retinal vein occlusion by injection of tissue plasminogen activator into a retinal vein" *Am. J Ophthalmol,* 1998; 126:142–44).

For example, some prior attempts have concentrated on using rigid boriscilicate glass or stainless steel micropipettes held either by hand or with a mechanical micromanipulator or robot. However, performing this task by hand is difficult because the pipettes are inflexible and must be held precisely within the lumen of the vessel (approximately 0.1 mm). Human tremor and involuntary motions make this extremely difficult. Short-term canulations using a high-resolution endoscope for increased intraoperative visibility has been demonstrated (Hazma H. S., Humayun M. S., Jensen P. S., Shelly T., Shoukas A. and De Juan E., Jr. "Endoscopic guided hand-held cannulation of the retinal veins in-vivo" *Invest Ophthalmol Vis. Sci. (abstract),* 1999) and successful longer-term cannulations of the retinal vessels have been reported numerous times using a micromanipulator and a rigid micropipette. (Alf B. E., de Juan E., Jr. "In vivo cannulation of retinal vessels" *Graefes Arch Clin. Exp. Ophthalmol,* 1987; 225:21–225; Gluckberg M. R., Dunn R., Giebs C. "In vivo micropuncture of retinal vessels" *Graefes Arch. Clin. Exp. Ophthalmol,* 1993; 231:405–407; Jensen P. S., Grace K. W., Attariwala R., Colgate J. E., Glucksberg M. R. "Toward robot-assisted vascular microsurgery in the retina" *Graefes Arch. Clin. Exp. Ophthalmol,* 1997; 235: 696–701; Weiss J. N., "Treatment of central retinal vein occlusion by injection of tissue plasminogen activator into a retinal vein" *Am. J. Ophthalmol,* 1998; 126:142–144). However, micromanipulators are complex, expensive and cumbersome to use in a surgical setting for the level of stability required. Further, micromanipulators also require that the head and eye of the patient be fixed with respect to the manipulator, typically accomplished by using eye rings, sutures, head straps, and other such physical restraints. Without such physical restraints, the infusion time allowed was relatively short (bolus injection). Further, even with such physical restraints, the rigid nature of the micropipettes used in these studies make it extremely difficult, if not impossible, to keep the tip of the pipette within the lumen of the vessel during the entire 30 minute drug delivery protocol. A micron scale motion of either the patient, the micropipette, the manipulator or the surgeon may cause the pipette to be dislodged.

Further, while these prior techniques demonstrate that vessel cannulation is possible in both laboratory and surgical settings using a mechanical manipulator (Weiss J. N., "Treatment of central retinal vein occlusion by injection of tissue plasminogen activator into a retinal vein" *Am. J. Ophthalmol,* 1998; 126:142–144), there is no technique to date that can be satisfactorily implemented in a surgical setting without these devices. Primary concerns are the cumbersome equipment required for cannulation and the lengthy infusion times associated with the thrombylitic therapy.

Thus, what is needed is a surgical device and method of use that allows infusion into a retinal vein for extended periods of time without the need for the surgeon, a robot, a micromanipulator or other holding devices to hold the surgical device in place during the infusion. What is further needed is a device that does not require rigidly fixating the eye to an eye ring during such long-term infusion. What is further needed is a device and method that may be suitably implemented in a surgical setting

SUMMARY OF THE INVENTION

The present invention provides a novel surgical device and methods for use thereof.

More particularly, the present invention provides a flexible microcatheter system that allows for infusion into a retinal vein for at least a period of time required for a bolus injection. Preferably, the present invention provides a flexible microcatheter system that allows for infusion into a retinal vein, without being held by hand, by a robot, by a micromanipulator or by similar holding means, for a period of time ranging from the time required for a bolus injection to at least 2 hours, more preferably at least 5 minutes, more preferably at least 10 minutes, more preferably at least 20 minutes, more preferably at least 30 minutes, more preferably at least 40 minutes, more preferably, at least 50 minutes, more preferably at least one hour, more preferably at least 1½ hours, and more preferably at least 2 hours.

The microcatheter system is particularly suitable for the treatment of retinal venous occlusive disease. In particular, the microcatheter system allows for the delivery of a thrombolytic locally at or near the site of the occluded retinal vein for the extended periods of time required for effective thrombolysis. The microcatheter system is easily positioned within a retinal vessel and remains stably within the vessel without being held by hand, by a robot, by a micromanipulator or by similar holding means.

When used herein, reference to the microcatheter system or cannula as "remaining within the vessel or vein" or "remaining stably within the vessel or vein" means that the microcatheter or cannula maintains a position within the vessel or vein that allows for the infusion of a solution through the microcatheter system or cannula and into the vessel or vein.

In a preferred embodiment, microcatheter system includes a flexible cannula for insertion into the retinal vein lumen. This cannula preferably has a sharp and rigid tip for easy retinal venous puncture. In a preferred embodiment, the tip of the cannula has a beveled ramp like tip configuration for easier insertion into the vessel. The body of the cannula is fabricated to be flexible and malleable to allow easy and stable positioning within a retinal vessel without being held by a robot, micromanipulator or similar holding means. Because the body of the cannula is flexible, it is capable of remaining within the retinal vessel for extended periods of time and is not as susceptible to patient or surgeon motions as a rigid cannula. Preferably, the flexible cannula is fabricated of polyimide or similar material. A particularly preferred material is 44 g polyamide tubing available from HV Technologies.

The flexible cannula is sized so as to be insertable into main tributaries of human retinal veins that are typically at least 100 µm in diameter. As such, the flexible cannula has an outer diameter no greater than 100 µm, preferably, from about 50 µm to about 80 µm, and more preferably, about 66 µm. The inner diameter of the cannula allows for sufficient flow of solution to the site of the occlusion. In most applications, the flow of solution to the site is at least about 0.2 cc/min of solution.

Due to the flexible, delicate nature of the flexible cannula, grasping the flexible cannula with forceps during insertion and positioning of the cannula within the retinal vein may crimp the cannula and render it useless. Thus, to facilitate insertion and manipulation within the eye, various protection means may be utilized.

In one embodiment, small wing-like extensions are mounted on the side of the flexible cannula. These wing-like extensions may be attached by, for example, a UV adhesive or similar attachment means. During manipulation and insertion of the cannula within the retinal vein, the wing-like extensions would be grasped by forceps or similar means.

In another embodiment, a metal portion may be mounted on the flexible cannula by, for example, epoxying the metal band to the cannula. The metal portion could then be grasped by forceps or by an electromagnet during manipulation and insertion of the cannula.

In another embodiment, a metal wire is mounted on the flexible cannula. During manipulation and insertion of the cannula within the retinal vein, the metal wire would be grasped by forceps or similar means.

In a particularly preferred embodiment, the microcatheter system has an intraocular portion that is composed of a hybrid of two different size cannulae. In addition to the above-described flexible cannula that is inserted into the retinal vein lumen, the microcatheter system further comprises a larger cannula encasing a portion of the small cannula. The larger cannula is less flexible than the smaller cannula, and may be grasped by forceps during manipulation and insertion of the cannula within the retinal vein, thereby protecting the flexible cannula. In a preferred embodiment, the larger cannula forms the part of the microcatheter system that is inserted just inside the eye and, as such, it provides the rigidity necessary to pass it into the eye without damage. The larger cannula preferably has an outer diameter ranging from about 400 µm to about 800 µm, and more preferably, about 556 µm. This larger cannula is sized so as to allow it to be easily attached to the tip of a syringe loaded with infusion fluid. The plunger of the syringe loaded with fluid may then be attached to a motorized pump for fluid injection. Preferably, both the smaller and larger cannulae are fabricated of polyimide or a similar material.

In a preferred embodiment, the flexible cannula and larger cannula are mounted inside a microcannula system, to ease the insertion of the cannulae through the sclera, as well as to help stabilize the cannulae throughout the procedure. Microcannula are well known and, thus, although described and shown with reference to a preferred embodiment, the general features (e.g. size, shape, materials) of the microcannula may be in accordance with conventional microcannulas. In a preferred embodiment, the microcannula system is constructed of a metal. Preferably, an inner plug, such as a silicone rubber inner plug, is further located on the microcannula system. The inner plug has an aperture through which the cannulae are inserted and which provides a fluid-tight seal about the cannulae to prevent leakage of fluid out of the eye through and around the cannulae. This allows for the non-traumatic insertion of the microcatheter while maintaining consent intraocular pressure.

The present invention also provides device kits, which preferably comprise one or more of the described microcatheter systems, preferably packaged in sterile condition.

Other aspects and embodiments of the invention are discussed infra.

BRIEF DESCRIPTION OF THE DRAWINGS

FIG. 1 is an isometric view of one embodiment of the surgical device in accordance with the present invention.

FIG. 2 is a side view of another embodiment of the surgical device in accordance with the present invention having wing-like extensions.

FIG. 3 is a side view of another embodiment of the surgical device in accordance with the present invention having a metal portion mounted on the cannula.

DETAILED DESCRIPTION OF THE INVENTION

Figure 4:
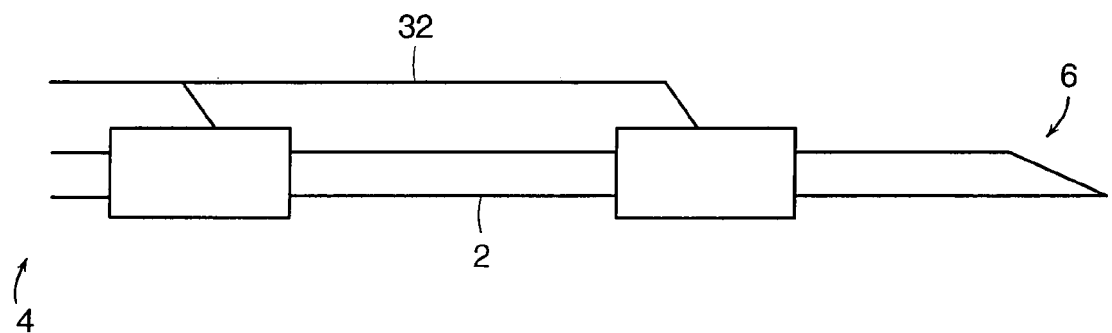
FIG. 4 is a side view of another embodiment of the surgical device in accordance with the present invention having a metal wire is mounted to the cannula.
Figure 5:
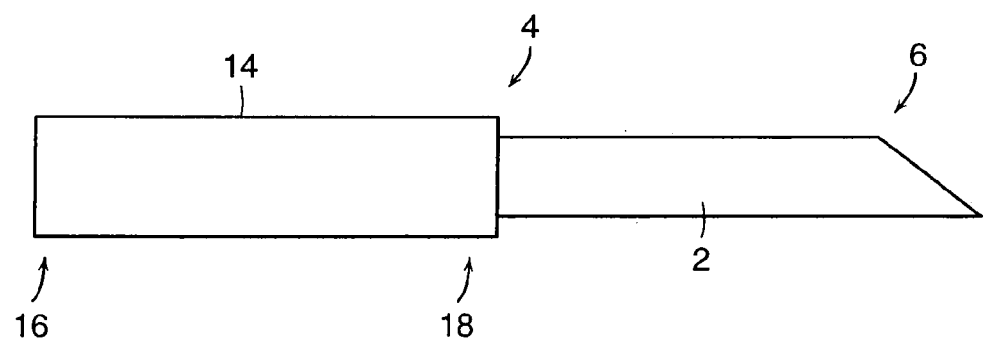
FIG. 5 is a side view of another embodiment of the surgical device in accordance with the present invention having a hybrid of two different sized cannulae.

Referring now to the various figures of the drawing, wherein like reference characters refer to like parts, there is shown in FIG. 1 various views of a surgical device (microcatheter system) 1, in accordance with the invention.

In a preferred embodiment, the surgical device 1 includes a cannula 2, having a proximal end 4 and a distal end 6. This cannula 2 is designed for insertion into main tributaries of human retinal veins that are typically at least 100 µm in diameter. As such, the cannula 2 has an outer diameter no greater than 100 µm, preferably, from about 50 µm to about 80 µm, and more preferably, about 66 µm.

As shown in FIGS. 1–5, the cannula 2 preferably has a sharp and rigid distal end 6 for easy retinal venous puncture. As shown in FIGS. 1–5, in preferred embodiments, the distal end 6 of the cannula 2 has a beveled ramp-like configuration for easy insertion into the retinal vessel. Preferably, the ramp-like distal end 6 has an angle of about 30°.

The surgical device 1 of the present invention is particularly suitable for the treatment of retinal venous occlusive disease. In particular, the surgical device 1 allows for the delivery of a thrombolytic locally at or near the site of the occluded retinal vein for the extended periods of time required for effective thrombolysis. Thus, the body of the cannula 2 is fabricated of a flexible and malleable material that provides stable positioning of the cannula 2 within a retinal vessel without requiring it to be hand-held and without requiring additional holding devices such as, for example, a robot or micromanipulator. Preferably, the body of the cannula 2 is fabricated of a flexible and malleable material that makes it less susceptible to patient or surgeon motions. Some suitable materials for fabricating the cannula 2 may include, for example, a variety of plastics used in fabricating flexible tubing. In a particularly preferred embodiment, the cannula 2 is fabricated of polyimide.

The thus formed surgical device allows for infusion into a retinal vein for at least a period of time required for a bolus injection without requiring it to be hand-held and without requiring additional holding devices such as, for example, a robot or micromanipulator. Preferably, the present invention provides a flexible microcatheter system that allows for infusion into a retinal vein for a period of time ranging for the time required for a bolus injection to at least 2 hours, more preferably at least 5 minutes, more preferably at least 10 minutes, more preferably at least 20 minutes, more preferably at least 30 minutes, more preferably at least 40 minutes, more preferably, at least 50 minutes, more preferably at least one hour, more preferably at least one and a half hours, and more preferably at least 2 hours, without requiring it to be hand-held and without requiring additional holding devices such as, for example, a robot or micromanipulator.

The inner diameter of the cannula 2 is sized to allow for sufficient flow of solution to the site of the occlusion. In most applications, the flow of solution to the site is at least about 0.2 cc/min of solution.

Due to the flexible, delicate nature of the cannula 2, grasping the cannula 2 directly, with forceps or similar grasping means, during insertion and positioning of the cannula 2 within the retinal vein may crimp and damage the cannula 2, which would limit or even prevent the flow of solution through the cannula 2. Thus, to facilitate insertion and manipulation of the cannula 2 within the eye, the surgical device 1 of the present invention may further comprise various protection means.

For example, in one embodiment shown in FIG. 2, one ore more small wing-like extensions 26 are mounted on the outer surface of the cannula 2. These wing-like extensions 26 may be attached by, for example, a UV adhesive or similar attachment means. During manipulation and insertion of the cannula 2 within the retinal vein, the wing-like extensions 26, rather than cannula 2, may be grasped by forceps or similar grasping means.

In another embodiment shown in FIG. 3, a metal portion 28 is mounted on the cannula 2 by, for example, epoxying the metal portion 28 to the cannula 2. The metal portion 28 could then be grasped by forceps or by an electromagnet 30 during manipulation and insertion of the cannula 2 Within the retinal vein.

In another embodiment shown in FIG. 4, a wire 32 is mounted on the cannula 2. During manipulation and insertion of the cannula 2 Within the retinal vein, the wire 30 may be grasped by forceps or similar grasping means.

In a preferred embodiment, the intraocular part of the microcatheter system is composed of a hybrid of two different size cannulae 2, 14. In addition to the above-described cannula 2 that is inserted into the retinal vein lumen, the microcatheter system further comprises a larger cannula 14 that encases a portion of the cannula 2.

In a preferred embodiment, the larger cannula 14 forms the part of the microcatheter system that is placed just inside the eye. The larger cannula 14 provides the rigidity necessary to pass it into the eye without damage and is less flexible than the smaller cannula 2. Preferably, the larger cannula 14 is fabricated of a plastic such as polyimide or a similar material. Because the smaller cannula 2 is delicate, it is preferred that when positioning the microcatheter system within the eye, one grasps the larger cannula 14 rather than the smaller cannula 2 which is more easily kinked and bent.

The larger cannula 14 has a proximal end 16 and a distal end 18. As shown in FIG. 1, a portion of the smaller cannula 2 is housed within the distal end 18 portion of the larger cannula 14. The proximal end 16 of the larger cannula 14 is preferably designed for attachment to the tip of a syringe loaded with infusion fluid. The plunger of the syringe may then be attached to a motorized pump or similar means for fluid injection over the duration of the thrombolysis procedure. In such an embodiment, the infusion fluid passes from the syringe, through the larger cannula 14, through the smaller cannula 2 and into the occluded retinal vessel. As such, the larger cannula 14 forms a fluid-tight seal about cannula 2 to prevent leakage of infusion fluid between the larger cannula 14 and cannula 2. In a preferred embodiment, the larger cannula 14 has an outer diameter that ranges from about 400 µm to about 800 µm, and, more preferably, about 556 µm.

Figure 6:
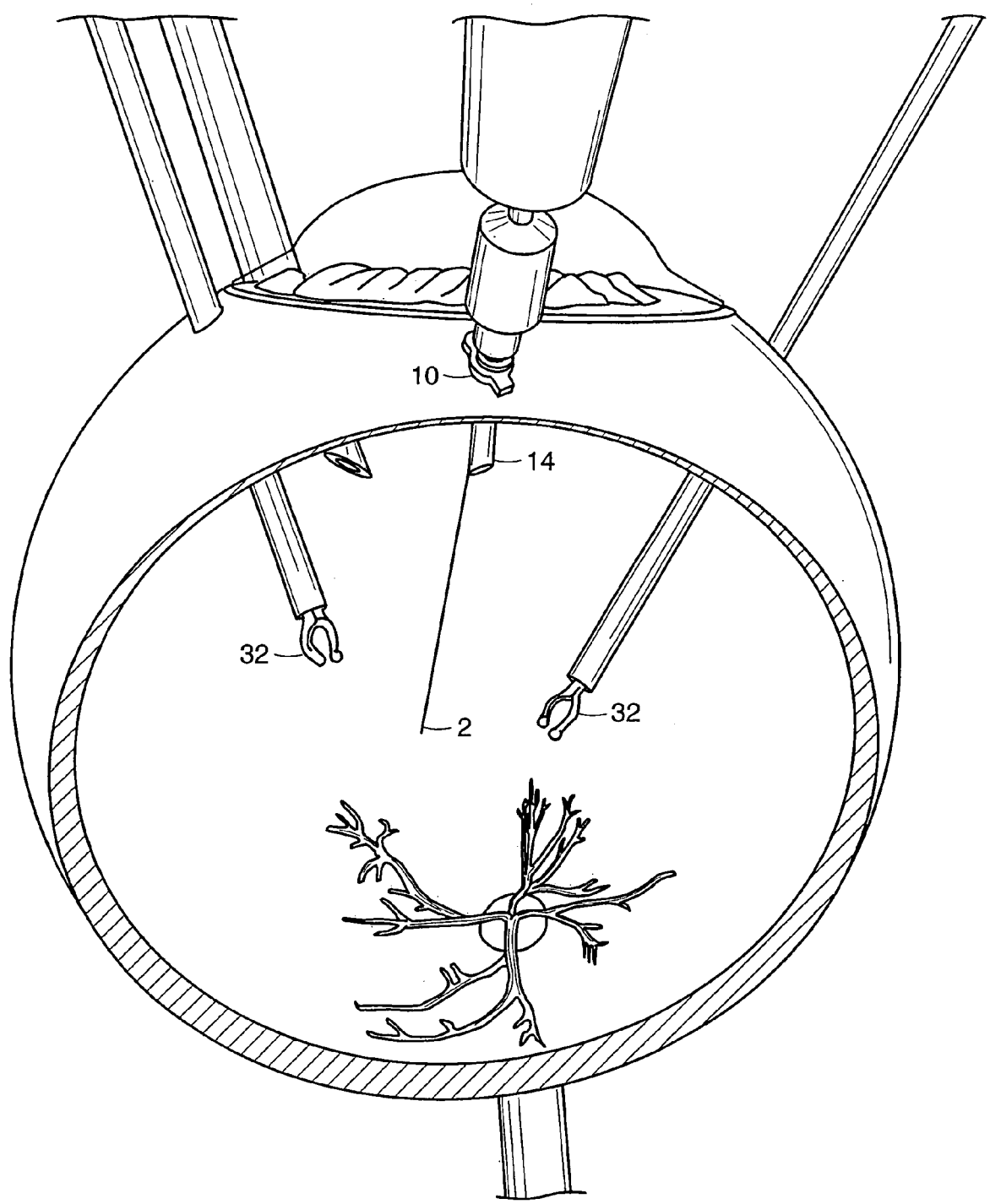
FIGS. 6–10 show schematic views of the surgical device being positioned within the eye for infusion into a retinal vein.
Figure 7:
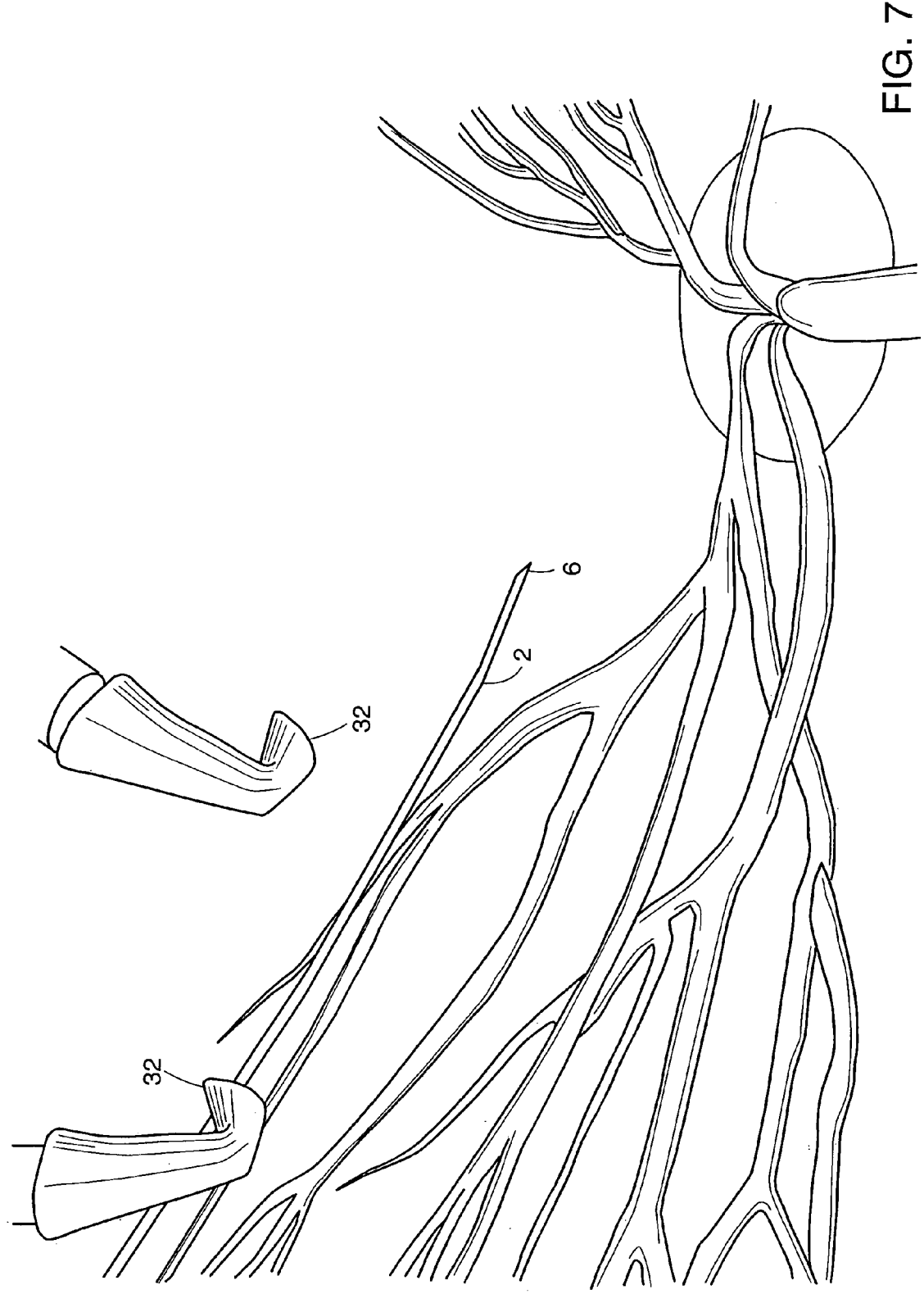
Figure 8:
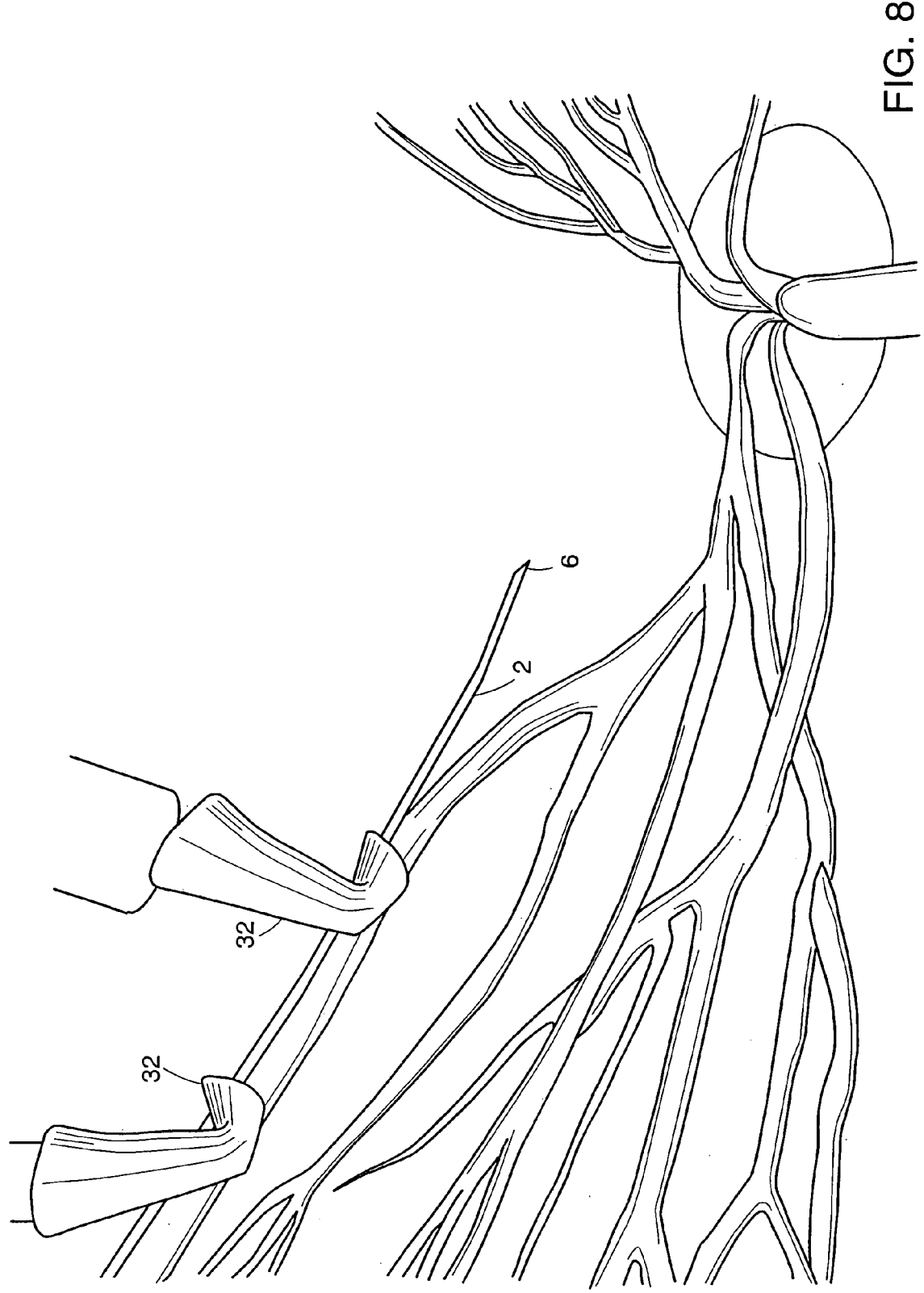
Figure 9:
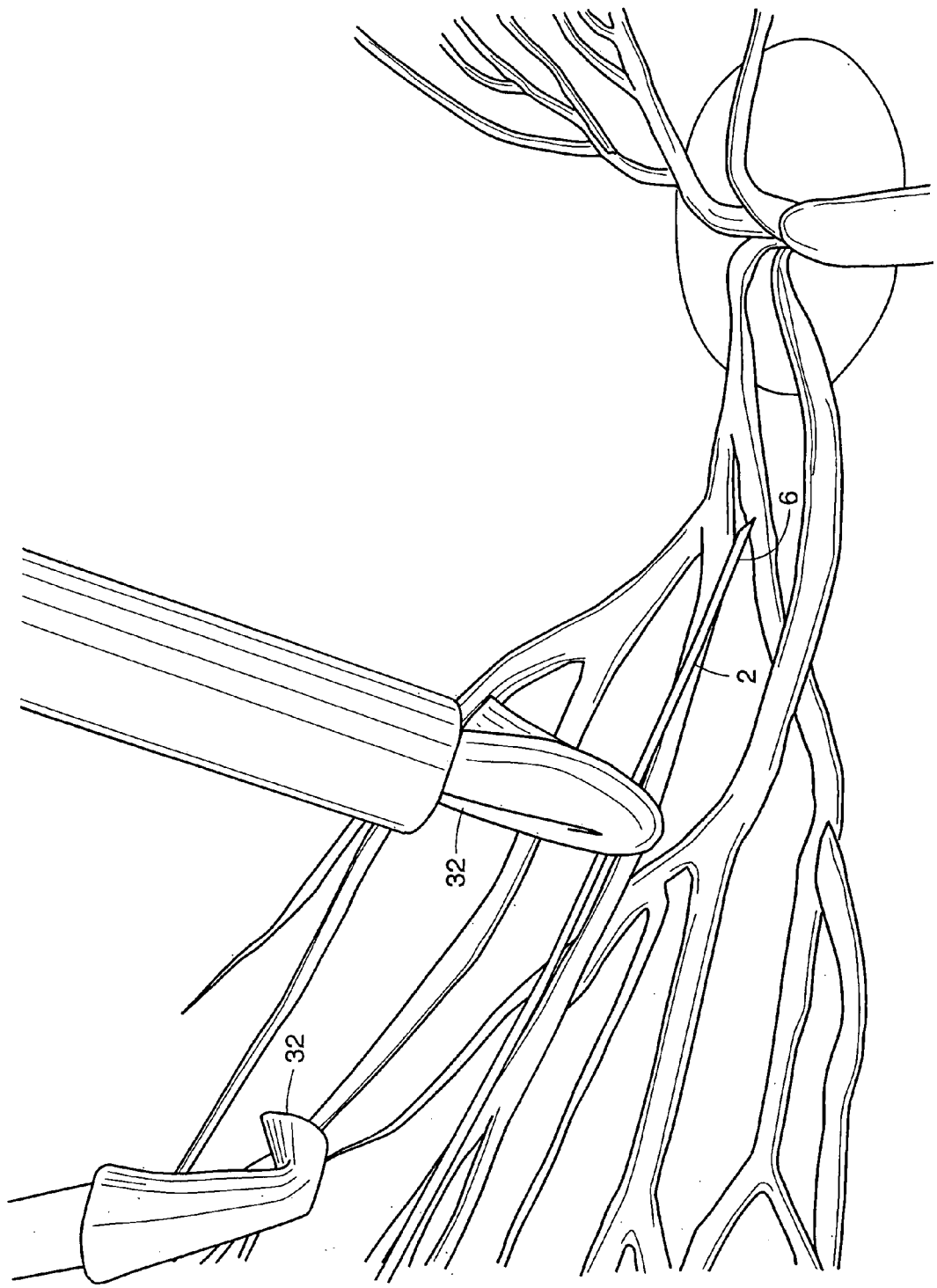
Figure 10:
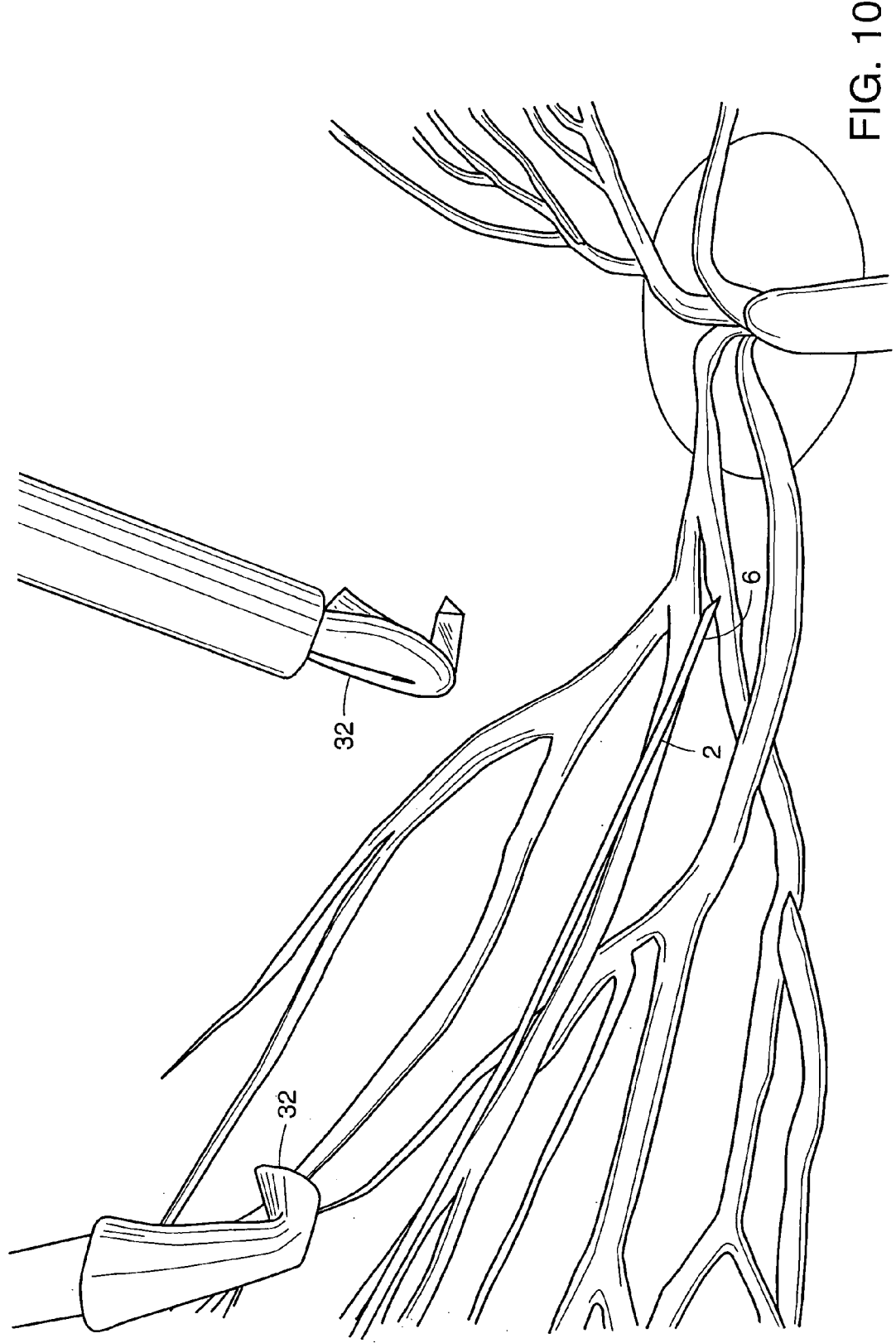

In a preferred embodiment, as shown in FIGS. 1 and 6, the cannulae 2, 14 are inserted into the eye through a modified microcannula system 10 that protects the cannulae 2, 14 during insertion through a sclerotomy. Microcannula are well known and, thus, the microcannula system 10 may be in accordance with conventional microcannulas.

Preferably, the modified microcannula system 10 is fabricated of a rigid material such as a metal. In use, and as shown in FIG. 6, the cannulae 2, 14 are inserted through and locked into the modified microcannula system 10, which may further act as a stable anchor site by preventing the transmission of inadvertent extraocular mechanical movements to the intraoculer microcatheter and, therefore, provides good stabilization of the microcatheter intraocularly.

Preferably, an inner plug 12 is located on the modified microcannula system 10. This inner plug 12 prevents leakage of fluid out of the eye through or around the cannulae 2, 14. In a preferred embodiment, the larger cannula 14 is inserted through this inner plug 12, and the inner plug 12 forms a seal around the cannula 14, which prevents leakage of fluid between the inner plug 12 and larger cannula 14. The inner plug, thus, has an aperture (not shown) through which the larger cannula 14 is inserted. This aperture forms fluid-tight seal about the outer diameter of the larger cannula 14 and, thus, has a diameter corresponding to the outer diameter of the larger cannula 14. If only a single cannula 2 is used without a second, larger cannula 14, the aperture would then form a fluid-tight seal about the outer diameter of the smaller cannula 2 and, thus, would have a diameter corresponding to the outer diameter of the smaller cannula 2 This combination of modified microcannula system 10 with cannulae 2, 14 and inner plug 12 allows for the non-traumatic insertion of the microcatheter while maintaining consent intraocular pressure. The inner plug 12 is preferably fabricated of silicone or a similar material which provides a proper seal around the cannula 2, 14.

The use of the microcatheter system of the present invention can be further understood from the following discussion relating to a method for treating retinal venous occlusive disease by vascular infusion into retinal veins and with reference to FIGS. 6–10. Reference also shall be made to FIGS. 1–5 for specific components or elements of the microcatheter system of the present invention not otherwise shown in FIGS. 6–10.

The microcatheterization technique in accordance with the present invention begins with a three-port pars plana vitrectomy. Next, vitrectomy with careful stripping of the posterior hyaloid face from the posterior pole is performed. After the vitrectomy, a fourth sclerotomy is created for insertion of the microcatheter system 1. It is important to choose the sclerotomy site such that the cannula 2 to be inserted into the eye is directly in-line (i.e. parallel) with the vein to be cannulated. FIG. 6 illustrates the schematic positioning of the intraocular instruments. If not in line with the vein to be cannulated, the undue torsional stress placed on the distal end 6 of the cannula 2 may result in inadvertent pulling out of the cannula 2 from the retinal venous lumen after an otherwise successful catheterization. An illuminated cannula 2 may be used to enhance visualization during bimanual manipulation of the microcatheter system 1.

Figure 11:
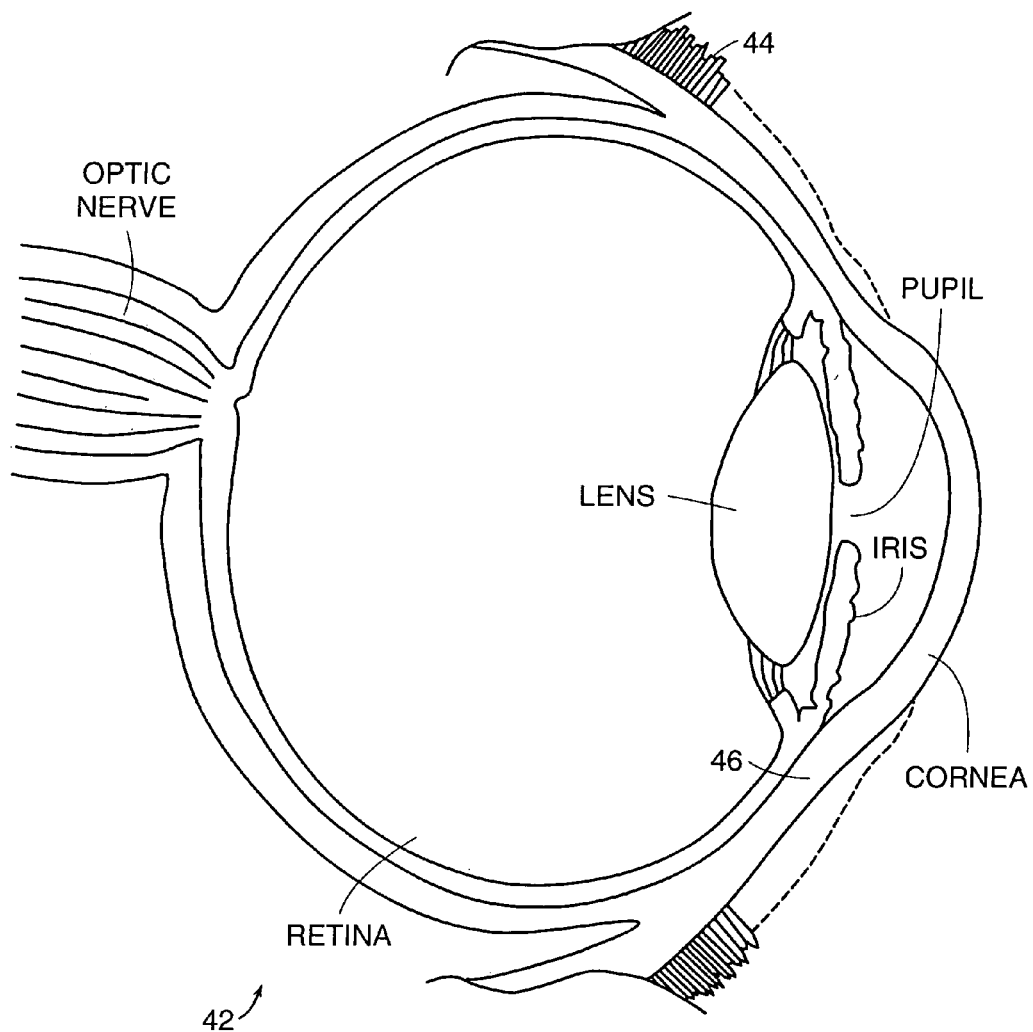
FIG. 11 is a cross-sectional schematic view of an eye illustrating one technique of pulling back of the conjunctiva to provide access into the eye for insertion of the surgical device of the present invention.

Conventional techniques may be used for the vitrectomy procedure and for creation of the fourth sclerotomy. Such techniques require the dissection of the conjunctiva 44 and the creation of pars plana scleral incisions through the sclera 46. As shown in FIG. 11, the dissection of the conjunctiva 44 typically involves pulling back the conjunctiva 44 about the eye 42 so as to expose large areas of the sclera 46 and the clipping or securing of the conjunctiva 44 in that pulled back state (normal position of conjunctiva shown in phantom). In other words, the sclera 46 is not exposed only in the areas where the pars plana scleral incisions are to be made. Surgical instruments used in the procedure are then passed through these incisions. Thus, the incisions created for the procedure must be made large enough to accommodate the instruments required for the procedure (typically 19 or 20 gauge, or approximately 1 mm in diameter).

Alternatively, the vitrectomy and creation of the fourth sclerotomy may be accomplished by use of an alignment device and method, such as that described in U.S. Ser. No. 09/523,767 the teachings of which are incorporated herein by reference, that enables sutureless surgical methods and devices therefore. In particular, such methods and devices do not require the use of sutures to seal the openings through which instruments are inserted. The alignment devices are inserted through the conjunctiva and sclera to form a plurality of entry apertures. Preferably, the alignment devices are metal or polyimide cannulas through which the surgical instruments used in the procedure are inserted into the eye.

Preferably, a 19 gauge or smaller metal cannula is inserted into the sclerotomy using, for example, a Grieshaber trocar system. The micrcannula system 10 is then loaded into the metal cannula and locked in place. The cannula 2 and larger cannula 14 may then be inserted by grasping the larger cannuls 14 by hand and gently threading the cannulae 2, 14 into the eye through the inner plug 12, which should now be residing within the lumen of the metal cannula. This maneuver will allow for the insertion of both cannula 2 and larger cannula 14 into the mid-vitreous cavity.

Once safely inside the eye, using microforceps 32, the distal end 6 of the smaller cannula 2 is directed towards the optic disc 36, as shown in FIGS. 1 and 7–10. Preferably, as shown in FIGS. 7–10, two microforceps 32 are used to more easily position the cannula 2 by passing the microcatheter system bock and forth between the microforceps 32, thereby optimizing the angle of approach. Both the angle and position of the cannula 2 are crucial to the success of the procedure. Specifically, the distal end 6 of the cannula 2 should be held at an angle that allows the distal end 6 to be oriented almost parallel to the vein. Preferably, only the dorsal portion of the microcatheter system 1 is held by the microforceps 32 to prevent the microforceps 32 from inadvertently contacting and damaging the underlying retina during the procedure.

The intraoculer pressure is preferably lowered to a level between about 5–10 mmHg, and the cannula 2 is inserted approximately 0.5–1 mm into the vessel and then released intravascularly. (FIGS. 9–10) Once inside the venous lumen, a controlled and continuous infusion of saline or thrombolytic solution is delivered by using an infusion pump set up in a similar configuration as that commonly used for silicone oil infusion.

After intravascular infusion for the desired period of time, the infusion bottle is raised and the cannula 2 is removed from the vessel. The elevated intraocular pressure is an effective tamponade and minimal bleeding extravasates from the small hole in the retinal venous wall.

The present invention also includes kits that comprise one or more microcatheter systems of the invention, preferably packaged in sterile condition. Kits of the invention also may be include a microcannula and alignment devices for use with the microcatheter system, e.g. such as a devices shown in FIGS. 1 and 6, preferably packaged in sterile condition, and/or written instructions for use of the microcatheter system and other components of the kit.

All documents mentioned herein are incorporated by reference herein in their entirety. The following non-limiting examples are illustrative of the invention.

EXAMPLES

Using the microcatheter system and surgical technique of the present invention, 12 of 15 enucleated porcine eyes and 7 of 7 in vivo canine eyes were catheterized. Once catheterized, intravenous infusion of saline was possible for the duration of the experiments in all eyes. This period of intravenous infusion ranged from 30 minutes to longer than 2 hours. On average, the present microcatheter system 1 and surgical technique allows for 0.2 cc/min of saline infused into the retinal vein via the microcatheter system 1 attached to an external motorized infusion pump.

Example 1

Enucleated Porcine Eyes Testing—Testing The Polyimide Tubing

In order to test the distal end 6 of cannula 2, enucleated porcine eyes were used. Twenty-two catheterization procedures were performed in twelve cadaveric porcine eyes. During these experiments, the anterior segment and the vitreous gel were removed. Four cuts were made in the sclera of the remaining posterior half of the globe and the sclera was pinned down to flatten the retina. The cannula was grasped at approximately 0.5 mm from the distal end 6 to be inserted into the vein. In order to make the distal end 6 of the cannula 2 sharp enough to penetrate the vein, the distal end 6 was cut using microscissors so that the tip would approximate a 30° ramp-like configuration. Under microscopic guidance, the distal end 6 of the cannula 2 punctured the vein wall and was advanced slightly within the lumen of the vein. The cannula was then released and the infusion pump activated to ascertain the intravascular status of the cannula 2.

The injected saline could be seen clearly traveling along the main tributaries of the retinal vein. Branch retinal veins and branch retinal arteries were cannulated at various distances from the optic disc (at first order vessel immediately after the central bifurcation; 1; 2; 3; and 4 disc diameters away from the optic disc). The major outcome measure in this model was the ability of the distal end 6 of the cannula 2 to both puncture retinal vessels and infuse fluid intravascularly at various distances from the optic disc.

In these experiments, catheterization of retinal veins was successfully performed. Overall, when polyimide tubing was used as the cannula 2, it could both puncture and promote intravenous injection of saline in 12 of 15 porcine eyes. In this model, the eyes were operated in an "open sky" setting, which allowed good visualization and greater amplitude of the movements within the eye. Conversely, the retinal veins in these cadaveric eyes were not completely filled with blood and had clotted blood from complete stagnation of blood flow, which might have made the procedure more difficult.

Example 2

In-Vivo Dog Eyes Testing—Developing the Microcatheter System & Surgical Technique In order to develop the surgical technique and delivery system to insert the microcatheter system inside the eye, seven eyes of seven dogs were operated on. The dog was selected as an animal model because the caliber of its retinal blood vessels and because the manner in which the vessels emanate from the optic disc are very similar to humans. All animal procedures were performed in accordance with both Johns Hopkins University Animal Care and Use Committee and the ARVO Statement for the Use of Animals in Ophthalmic and Vision Research.

The dogs were anesthetized initially with Telasol (Tiletamine HCl and Zolazepam HCl, Fort Dodge Animal Health; 4–7.5 mg/kg IM) and then they received a gas mixture with oxygen and halothane (98–99% oxygen and 1–2% halothane at a rate of 1.5–2 l/min). Throughout the surgery the dog's EEG, respiration rate and body temperature were monitored. The operated eye was dilated using phenylephrine (10%) and tropicamide (1%). A standard 3-port vitrectomy with posterior hyaloid striping was performed while viewed through an operating microscope and a surgical contact lens sutured to the sclera. Before the creation of a fourth sclerotomy through which the cannulae 2, 14 were to be inserted, the preferential venous puncture site was selected. The retinal vein catheterization was performed as described herein. The retinal veins were catheterized at various distances from the optic disc, ranging from 1 to 4 disc diameters away from the disc, and direct visualization of intravascular flow of the injected fluid was used to indicate the intravascular status. In four eyes saline solution was used and in the other three eyes tissue plasminogen activator was used (t-PA, Genentech, Inc., San Francisco, Calif., USA) as a 2 mg/cc solution.

The major outcome measure was the ability to influx saline or t-PA solution in a constant and stable fashion into the retinal vein for a period of at least 30 minutes. After the infusion, the distal end 6 of the cannula 2 was removed from the vessel lumen.

Other parameters studied were (a) the ability of the microcatheter system to remain intravascularly either after increased pressure given by the infusion pump or after intentional agitated movements of the eye, (b) the amount of hemorrhage during and after the procedure, and (c) the re-establishment of the blood flow upon withdraw of the microcatheter.

In these experiments, using the microcatheter system in an in-vivo setting, cannulation and injection of solution into the retinal veins in all 7 living dogs eyes for a period of at least 30 minutes was successful. For each retinal vein catheterization approximately 1 to 6 puncture attempts were made before succeeding. The main challenge was to hold the microcatheter in an appropriate angle and position for the puncture procedure. In all eyes with this living model, after successful venous puncture, the continuous intravenous injection of saline or t-PA. solution resulted in a visible flow of the infused fluid towards the optic disc. With the average pressure of 40 psi in the 10 cc-syringe used to infuse the saline intravascularly, which was being controlled by an infusion pump, the injected flow achieved was approximately 0.2 cc/min. Despite increasing the infusion pump pressure up to 65 psi, the microcatheter remained in its intravascular position, albeit the rate of infusion into the retinal veins did not increase noticeably. The microcatheter remained intravenously even after intentional shaken movements of the eye. A very small amount of bleeding occurred at the puncture site upon the microcatheter withdrawl, which was easily controlled by raising the infusion bottle. In all three living dogs' eyes in which t-PA solution was infused intravenously, no significant increase in hemorrhage was observed. In all eyes, the blood flow was immediately re-established after microcatheter removal without indication of obstructive thrombus formation at the penetration site.

The foregoing description of the invention is merely illustrative thereof, and it is understood that variations and modifications can be effected without departing from the scope or spirit of the invention as set forth in the following claims.

What is claimed is:

1. A microcatheter system for infusion of a solution into a retinal vein, wherein the microcatheter system remains within the retinal vein during the infusion without an external holding device for at least a period of time required for a bolus injection, comprising:
a flexible cannula mounted in a second cannula, at least a portion of the second cannula, configured to be disposed within the eve when the microcatheter system is placed within the eye for infusion into a retinal vein, at least a portion of the flexible cannula, configured to be disposed within the retinal vein when the microcatheter system is placed within the eye for infusion into a retinal vein, wherein the flexible cannula and the second cannula form an infusion fluid path and wherein the flexible cannula has an outer diameter less than about 100 µm.

2. A microcatheter system comprising:
a flexible cannula configured for insertion into a retinal vein lumen, the flexible cannula having an outer diameter less than about 100 µm, whereby a solution is infused into the retinal vein lumen through the flexible cannula and the flexible cannula remains within the retinal vein lumen during the infusion without an external holding device for at least a period of time required for a bolus injection; and
a second cannula configured to be disposed within the eye when the flexible cannula is inserted into a retinal vein, wherein the microcatheter system comprises the flexible cannula at least partially encased in the second cannula, wherein the flexible cannula and the second cannula form an infusion fluid path.

3. A microcatheter system comprising:
a flexible cannula for insertion into a retinal vein lumen, the flexible configured cannula having an outer diameter less than about 100 µm, whereby a solution is infused into the retinal vein lumen through the flexible cannula and the flexible cannula remains within the retinal vein lumen during the infusion without an external holding device; and
a second cannula configured to be disposed within the eve when the flexible cannula is inserted into a retinal vein, wherein the microcatheter system comprises the flexible cannula mounted in the second cannula, wherein the flexible cannula and the second cannula form an infusion fluid path.

4. The microcatheter system of any one of claims 1 through 3, wherein solution is infused at a flow rate of at least about 0.2 cc/mm.

5. The microcatheter system of any one of claims 1 through 3, wherein the microcatheter system comprises a flexible cannula for insertion into a retinal vein lumen, the flexible cannula having a proximal end and a distal end and the distal end is sharp and rigid for puncturing the retinal vein lumen.

6. The microcatheter system of claim 5, wherein the distal end has a beveled ramp-like shape.

7. The microcatheter system of claim 6, wherein the ramp-like distal end forms an angle of about 30°.

8. The microcatheter system of any one of claims 1 through 3, wherein the flexible cannula is fabricated of polyimide.

9. The microcatheter system of any one of claims 1 through 3, wherein the flexible cannula has an outer diameter of from about 50 µm to about 80 µm.

10. The microcatheter system of claim 9, wherein the flexible cannula has an outer diameter of about 66 µm.

11. The microcatheter system of any one of claims 1 through 3, further comprising a second cannula having a larger diameter than the flexible cannula.

12. The microcatheter system of claim 11, wherein the second cannula is less flexible than the flexible cannula.

13. The microcatheter system of claim 11, wherein second cannula has a proximal end and a distal end, and a portion of the flexible cannula is housed within the distal end of the second cannula.

14. The microcatheter system of claim 13, wherein the second cannula forms a fluid-tight seal about the flexible cannula.

15. The microcatheter system of claim 11, wherein the proximal end of the second cannula is sized for attachment to the tip of a syringe through which solution is infused.

16. The microcatheter system of claim 11, wherein the second cannula has an outer diameter that ranges from about 400 µm to about 800 µm.

17. The microcatheter system of claim 16, wherein the second cannula has an outer diameter of about 556 µm.

18. The microcatheter system of claim 11, further comprising a modified microcannula system in which the flexible cannula and second cannula are mounted.

19. The microcatheter system of any one of claims 1 through 3, wherein the microcannula system further includes an inner plug mounted on the modified microcannula system and the inner plug is fabricated of silicone.

20. The microcatheter system of any one of claims 1 through 3, wherein the microcannula system further includes an inner plug mounted on the modified microcannula system and the inner plug has an aperture through which the second cannula and flexible cannula are inserted.

21. The microcatheter system of any one of claims 1 through 3, wherein the microcannula system further includes an inner plug mounted on the modified microcannula system and the inner plug forms a fluid-tight seal about the second cannula.

22. The microcatheter system of any one of claims 1 through 3, wherein the flexible cannula is illuminated for enhanced visibility.

23. The microcatheter system of any one of claims 1 through 3 wherein the microcatheter system or flexible cannula remains within the retinal vein during the infusion without an external holding device for a period of time of at least 5 minutes.

24. The microcatheter system of claim 23, wherein the period of time is at least 10 minutes.

25. The microcatheter system of claim 24, wherein the period of time is at least 20 minutes.

26. The microcatheter system of claim 25, wherein the period of time is at least 30 minutes.

27. The microcatheter system of claim 26, wherein the period of time is at least 40 minutes.

28. The microcatheter system of claim 27, wherein the period of time is at least 50 minutes.

29. The microcatheter system of claim 28, wherein the period of time is at least one hour.

30. The microcatheter system of claim 29, wherein the period of time is at least one and a half hours.

31. The microcatheter system of claim 30, wherein the period of time is at least two hours.

32. A medical device kit, comprising one or more of the microcatheter systems of any one of claims 1 through 3.

33. The kit of claim 32 wherein the one or more microcatheter systems are packaged in sterile condition.

34. The microcatheter system of any one of claims 1 through 3, wherein the flexible cannula comprises a flexible body and a rigid tip for puncturing the retinal vein lumen.

35. The microcatheter system of claim 34, wherein at least a portion of the rigid tip is disposed within the retinal vein when the second cannula is disposed within the eye.

36. A method for manual retinal vein catheterization comprising inserting a microcatheter system within a retinal vein and infusing solution into the retinal vein, whereby the microcatheter system remains within the retinal vein without an external holding device, wherein the microcatheter system comprises a flexible cannula mounted in a second cannula, wherein the flexible cannula and the second cannula form an infusion fluid path.

37. The method of claim 36, wherein solution is infused at a flow rate of at least about 0.2 cc/mm.

38. The method of claim 36, further comprising inserting a metal cannula into an incision in the eye prior to inserting the microcatheter system into the eye, whereby the microcatheter system is inserted into the eye through the metal cannula.

39. The method of claim 38, further comprising insertion of a microcannula through the metal cannula, wherein the microcatheter system is inserted into the eye through the metal cannula.

40. The method of claim 36, further comprising the step of making four sclerotomies in the eye, whereby two microforceps are inserted in two of the sclerotomies and the microcatheter system is inserted into the eye through the fourth sclerotomy.

41. The method of claim 40, wherein the fourth sclerotomy site is made such that the microcatheter system is inserted into the eye with the flexible cannula approximately parallel to the retinal vein.

42. The method of claims 40 or 41, further comprising the step of using the microforceps to direct the flexible cannula towards the optic disc of the eye.

43. The method of claim 40, further comprising the steps of passing the microcatheter system back and forth between the microforceps to position the microcatheter system so that the distal end of the flexible cannula is approximately parallel to the retinal vein.

44. The method of claim 36, wherein the microcatheter system further comprises a second cannula having a larger diameter than the flexible cannula, the second cannula having a proximal end and a distal end, whereby a portion of the flexible cannula is housed within the distal end of the second cannula.

45. The method of claim 44, wherein the proximal end of the second cannula is attached to the tip of a syringe through which solution is infused, and the second cannula forms a fluid-tight seal about the flexible cannula.

46. The method of claim 36, wherein the microcatheter system or flexible cannula remains within the retinal vein during the infusion without an external holding device for a period of time of at least 5 minutes.

47. The method of claim 46, wherein the period of time is at least 10 minutes.

48. The method of claim 47, wherein the period of time is at least 20 minutes.

49. The method of claim 48, wherein the period of time is at least 30 minutes.

50. The method of claim 49, wherein the period of time is at least 40 minutes.

51. The method of claim 50, wherein the period of time is at least 50 minutes.

52. The method of claim 51, wherein the period of time is at least one hour.

53. The method of claim 52, wherein the period of time is at least one and a half hours.

54. The method of claim 53, wherein the period of time is at least two hours.

* * * * *